United States Patent [19]

Lajus

[11] Patent Number: 4,741,014
[45] Date of Patent: Apr. 26, 1988

[54] RADIOLOGICAL INSTALLATION HAVING A SINGLE RECEIVER

[75] Inventor: Pierre C. Lajus, Meudon, France
[73] Assignee: Thomson-CGR, Paris, France
[21] Appl. No.: 684,468
[22] Filed: Dec. 21, 1984

[30] Foreign Application Priority Data

Jan. 3, 1984 [FR] France ............................. 84 00036

[51] Int. Cl.⁴ .............................................. H01J 31/49
[52] U.S. Cl. ..................................... 378/189; 378/167; 378/177
[58] Field of Search ............... 378/189, 195, 196, 177, 378/179, 167

[56] References Cited

U.S. PATENT DOCUMENTS

| | | | |
|---|---|---|---|
| 2,508,449 | 5/1950 | Davis, Jr. et al. | 378/179 |
| 2,582,776 | 1/1952 | Greenberg et al. | 378/190 |
| 3,325,643 | 6/1967 | Craig et al. | 378/189 |
| 4,019,061 | 4/1977 | Finkenzelles et al. | 378/177 |
| 4,334,155 | 6/1982 | Gieschen et al. | 378/196 |
| 4,365,344 | 12/1982 | Dornheim | 378/189 |

FOREIGN PATENT DOCUMENTS 2158649 6/1973 France .
797297 7/1958 United Kingdom .

OTHER PUBLICATIONS

"Diagnostic X-Ray System Compatible with DHEW Standards", Nakajima et al., *Toshiba Review*, No. 110, Jul.-Aug. 1977, pp. 14-17.

*Primary Examiner*—Janice A. Howell
*Assistant Examiner*—David P. Porta
*Attorney, Agent, or Firm*—Roland Plottel

[57] ABSTRACT

A radiological installation for front and profile examinations using a single image receiver. The receiver is fixed to a transverse arm with respect to the table by means of a rotation shaft which may be locked in at least two predetermined positions, said arm forming part of a mobile support movable along said table.

8 Claims, 3 Drawing Sheets

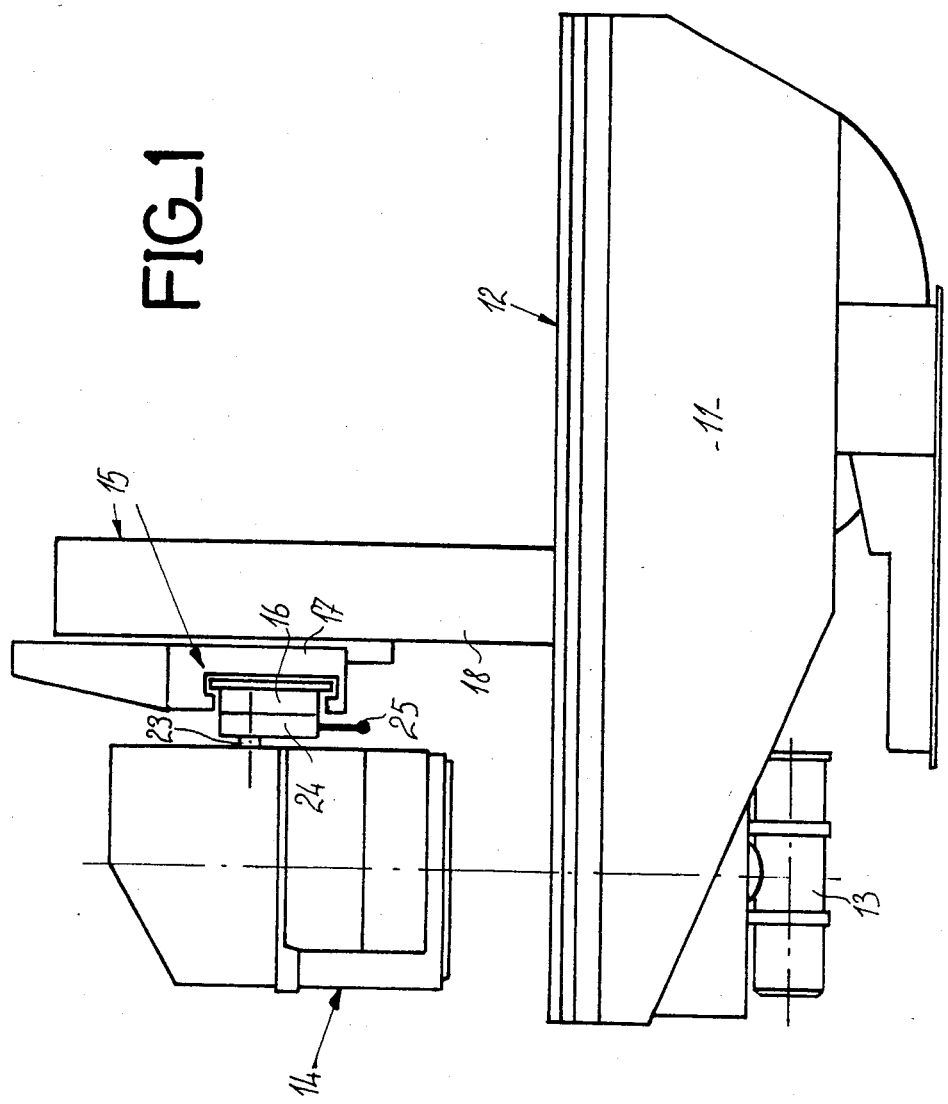

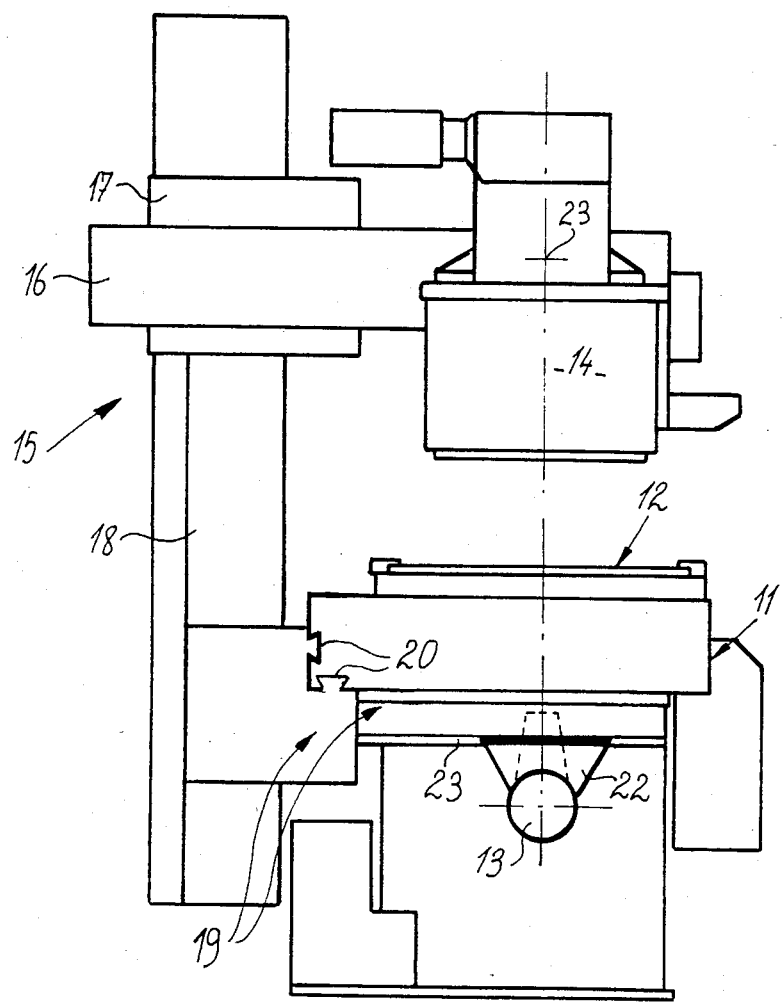
FIG_2

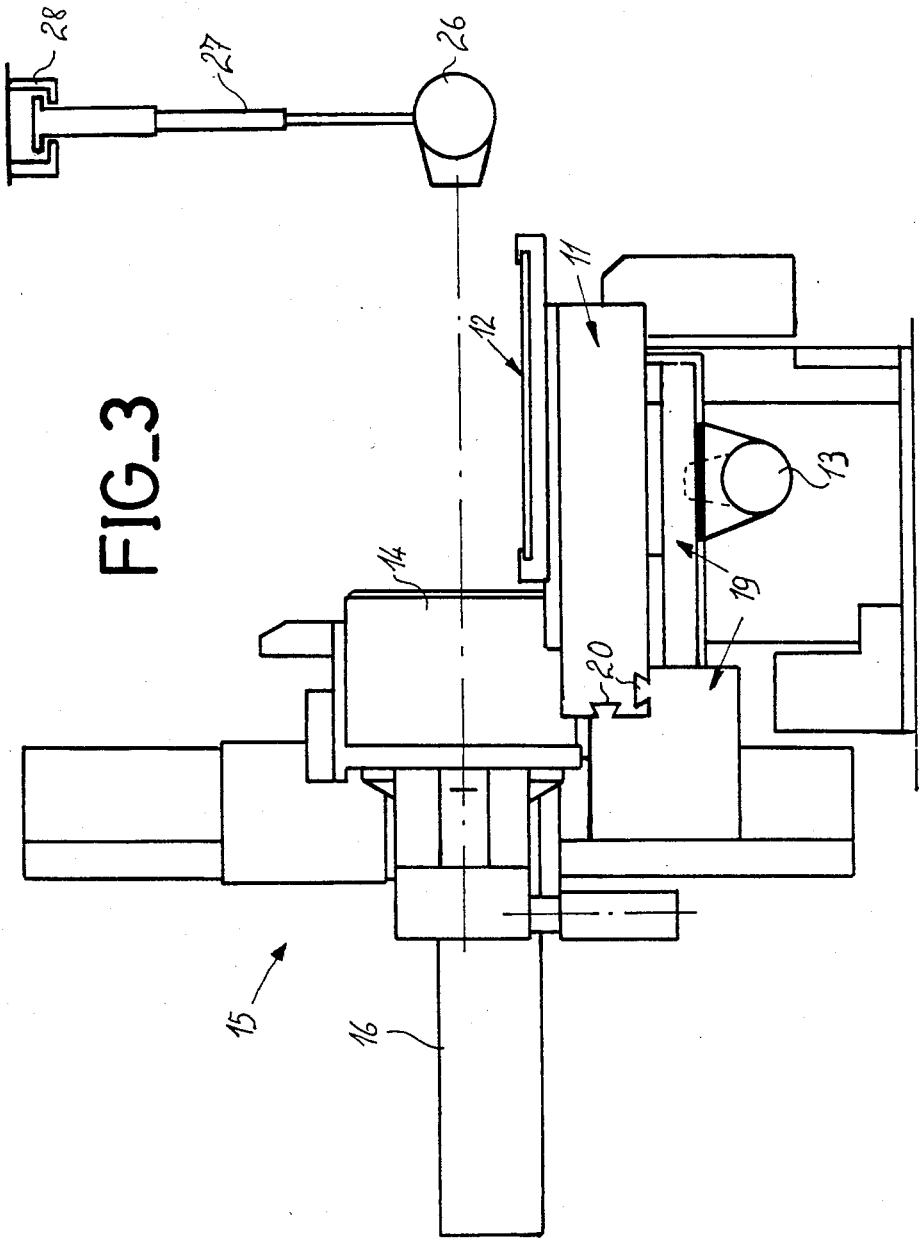

RADIOLOGICAL INSTALLATION HAVING A SINGLE RECEIVER

BACKGROUND OF THE INVENTION

The present invention relates to a radiological installation having a single receiver; more particularly, the invention relates to such an installation providing more especially front and profile radiological observations by means of a single image receiver, using simple mechanical means well adapted to be associated with a tilting examination table.

In radiological installations, luminance amplifiers are more widely used as receiver. These devices in fact have the advantage of being able to be read by means of a television camera, which, after digitilization of the video signal and digital processing of the images (logarithmic image subtraction, in particular) gives images of exceptional contrast and clearness. Luminance amplifiers are still relatively heavy and space consuming so that incorporation thereof in a radiological installation often causes problems. Furthermore, it is an expensive subassembly of the installation.

Among the possibilities of use which it is desirable to offer the doctor, may be mentioned principally the possibility of carrying out front or profile radiological examinations and also the fact of having a tilting examination table. The invention satisfies these requirements, in a particularly simple and economical way, because in particular it only uses one receiver.

SUMMARY OF THE INVENTION

To this end, the invention provides mainly a radiological installation comprising an examination table, an X ray source and an image receivr mounted on a mobile support, wherein at least one arm of said support is movable transversely with respect to said table and said receiver is mounted on said arm by means of a rotation shaft which can be locked in at least two predetermined positions.

This arrangement allows the double front and profile examination. Of course, the structure which has just been described above may be associated with a tilting examination table, known per se, the above mobile support being secured to said tilting table so as to be able to move longitudinally with respect thereto. It should further be noted that the installation thus defined as a triple access (one of the longitudinal sides of the table and the two ends thereof) which is particularly advantageous for the user.

BRIEF DESCRIPTION OF THE DRAWINGS

The invention will be better understood and other advantages will be better understood from the following description of a radiological installation constructed in accordance therewith, which description is given solely by way of example with reference to the accompanying drawings in which:

FIG. 1 is a general elevational view of an installation according to the invention;

FIG. 2 is a view along arrow II of FIG. 1, showing the different elements in position for a front radiological examination;

FIG. 3 is a view similar to that of FIG. 2, showing the elements in position for a profile radiological examination.

DESCRIPTION OF THE PREFERRED EMBODIMENT

Referring to the drawings, the installation is formed essentially of an examination table 11 having a patient supporting surface 12, a first X ray source 13 and an image receiver 14 carried by a mobile support 15. The examination table 11 is advantageously (but not exclusively) a tilting table known per se. In the embodiment shown the patient supporting surface is a rigid panel, but a more or less concave surface could be easily provided defining a sort of bed. The image receiver may for example be a conventional luminance amplifier. The mobile support 15 comprises an arm 16 movable transversely with respect to table 11 and, for that, is compelled to move in guide means defined in a carriage 17. This latter is compelled to move along a guide column 18 fastened to the table and disposed on a longitudinal side thereof, substantially perpendicular to the patient supporting surface. A lower extension 19 of this column cooperates with dove tail slides 20 (or any other equivalent system) fixed to the table and disposed longitudinally. Thus, the mobile support assembly 15 carrying receiver 14 follows the tilting movement of table 11. All the different relative movements between receiver 14, arm 16, carriage 17, column 18 and the table are preferably controlled by electric motors associated with conventional servo-control positioning systems, which are not described for they do not form part of the invention. Balanced manual moving systems may also be provided.

The X ray source 13 integrated in table 11 is mounted for longitudinal movement in the tilting structure of the examination table. Advantageously, it may be mounted on the lower extension 19 of column 18 so as to follow the longitudinal movements of receiver 14. In the example, the X ray source 13 is also movable transversely so as to follow the transverse movements of the image receiver. For that, it is fixed to an intermediate support 22 movable in slides 23 of said lower extension 19 of column 18. Preferably, a servo-controlled positioning system is provided between the control means for arm 16 and those for the intermediate support 22. Source 13 is orientated so that the axis of the x ray beam is substantially perpendicular to the patient supporting surface 12, that is to say continually centered with respect to receiver 14 (taking account of the above defined related movements) when this latter is in a predetermined position, with respect to arm 16 (FIGS. 1 and 2) that is to say facing the table.

According to an important feature of the invention, receiver 14 is mounted on arm 16 by means of a rotation shaft 23 which may be locked in at least two predetermined positions. One of these positions is the one which places the receiver in the position shown in FIGS. 1 and 2. The other position, at 90° from the preceding one, is that which places the receiver in the position shown in FIG. 3. Shaft 23 is journalled for example in a bearing device 24, fixed to arm 16 and comprising locking means controlled by a lever 25. Device 24 may also comprise an electric motor controlling the rotation of shaft 23. The position of this latter with respect to receiver 14 is chosen so as to approximate as well as possible the indifferent balancing of receiver 14 with respect to shaft 23, for facilitating handling thereof particularly in the case where it is not motor assisted.

Thus, with this arrangement, receiver 14 may occupy another lateral position (FIG. 3) with respect to the table, by pivoting the receiver through 90° with respect to arm 16 accompanied by transverse withdrawal of this latter and lowering of the carriage 17. A second x ray source 26 fastened to a mobile support independent of the table may then be approached by this latter for providing a radiological profile examination. A telescopic suspension 27 may for example be provided movable in a rail 28 fixed to the ceiling of the radiology room.

What is claimed is:

1. A radiological installation comprising an examination table having a patient supporting surface, a mobile support carried by said examination table, an X-ray source and a image receiver mounted on said mobile support, said mobile support comprising a guide column fastened to sadi examination table and disposed on a longitudinal side thereof and substantially perpendicular to said patient supporting surface, a carriage supported for movement along said guide column, said mobile support having an arm which is movable linearly and transversely with respect to said table and with respect to said column, said carriage supporting said arm which supports said receiver, said receiver being mounted on said arm by means of a rotation shaft which may be locked in at least two predetermined positions, said two predetermined positions allowing respectively front radiological examinations and profile radiological examinations of a patient lying on the patient supporting surface, said receiver being above the patient supporting surface for the front radiological examinations.

2. The installation as claimed in claim 1 wherein said examination table is a tilting table.

3. The installation as claimed in claim 1 wherein said guide column has a lower extension which cooperates with at least one slide fixed to said table and arranged longitudinally.

4. The radiological installation as claimed in claim 1, comprising an X-ray source mounted on a mobile support for emitting a beam substantially perpendicular to said table opposite said receiver when said receiver is in a position which corresponds to one of said predetermined positions of said rotation shaft.

5. The installation as claimed in claim 1 comprising a first X-ray source integrated in the table under said patient supporting surface and orientated so that the axis of the beam is substantially perpendicular to said patient supporting surface and a second X-ray source fixed to another mobile support independent of said table.

6. The installation as claimed in claim 3 comprising a first X-ray source integrated in the table under said patient supporting surface and orientated so that the axis of the beam is substantially perpendicular to said patient supporting surface and a second X-ray source fixed to another mobile support independent of said table, and wherein said first X-ray source is mounted for longitudinal movement in the tilting structure of said examination table.

7. The installation as claimed in claim 6 wherein said first X-ray source is mounted on said lower extension of said column and moves therewith.

8. The installation as claimed in claim 6 wherein said first X-ray source is fixed to an intermediate support movable in the transverse slides of said lower extension.

* * * * *